United States Patent [19]

Goldstein

[11] Patent Number: 4,597,386
[45] Date of Patent: Jul. 1, 1986

[54] LUMBAR SUPPORT SYSTEM
[76] Inventor: Morton I. Goldstein, 2658 E. Broad St., Columbus, Ohio 43209
[21] Appl. No.: 581,710
[22] Filed: Feb. 21, 1984
[51] Int. Cl.⁴ .......................... A61F 5/02; A47C 7/02
[52] U.S. Cl. ........................................ 128/78; 5/432; 297/284; 297/460
[58] Field of Search .................... 128/70, 75, 78, 30.2, 128/33; 5/432, 433, 462, 464; 297/230, 231, 284, 460

[56] References Cited
U.S. PATENT DOCUMENTS
4,431,232 2/1984 Hannouche ...................... 297/284 X
4,471,993 9/1984 Watson ................................ 297/230

FOREIGN PATENT DOCUMENTS
1590583 6/1981 United Kingdom .................... 5/432

Primary Examiner—Richard J. Apley
Assistant Examiner—Alan W. Cannon
Attorney, Agent, or Firm—Robert B. Watkins

[57] ABSTRACT

A portable apparatus and system for supporting the lumbar lordosis region of the back of a human being including a panel and cushion assembled in supporting contact, with the panel being flexibly formed in the transverse shape of a columnar beam providing rigidity on the longitudinal axis of lumbar lordosis of the human being.

14 Claims, 11 Drawing Figures

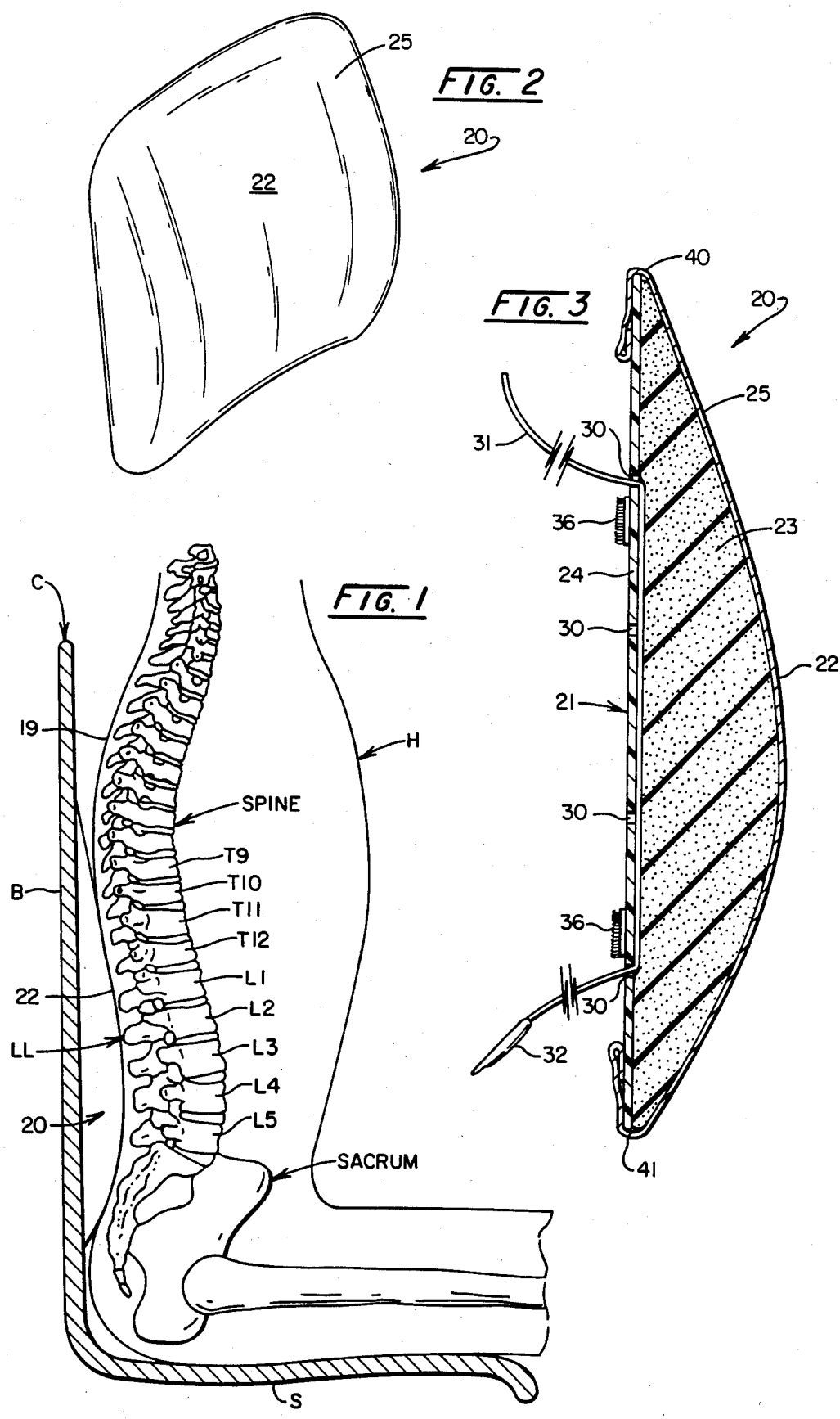

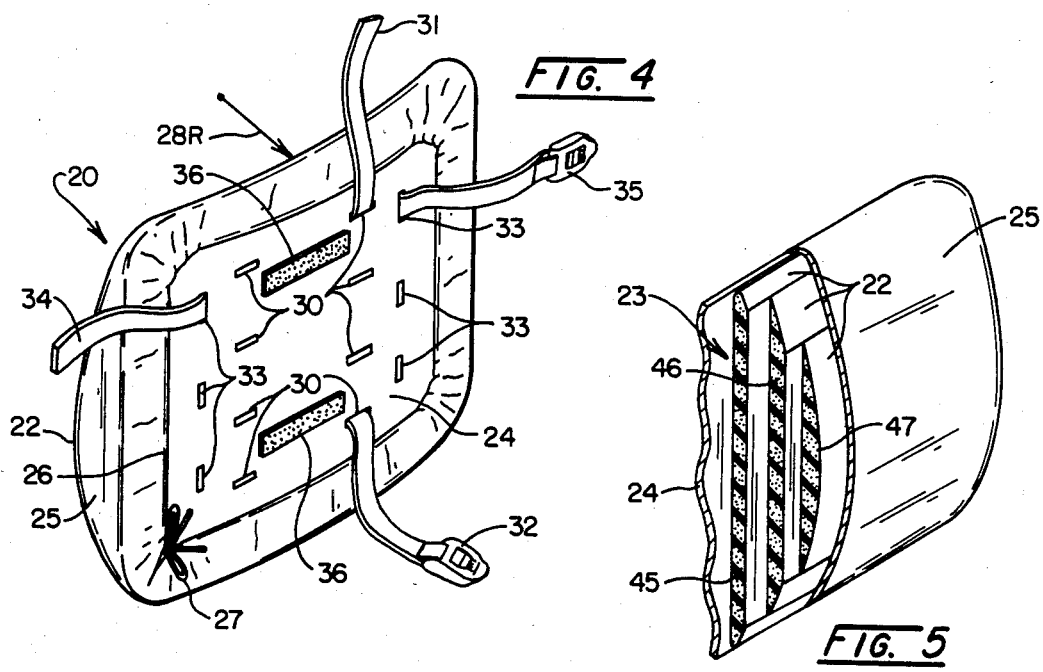
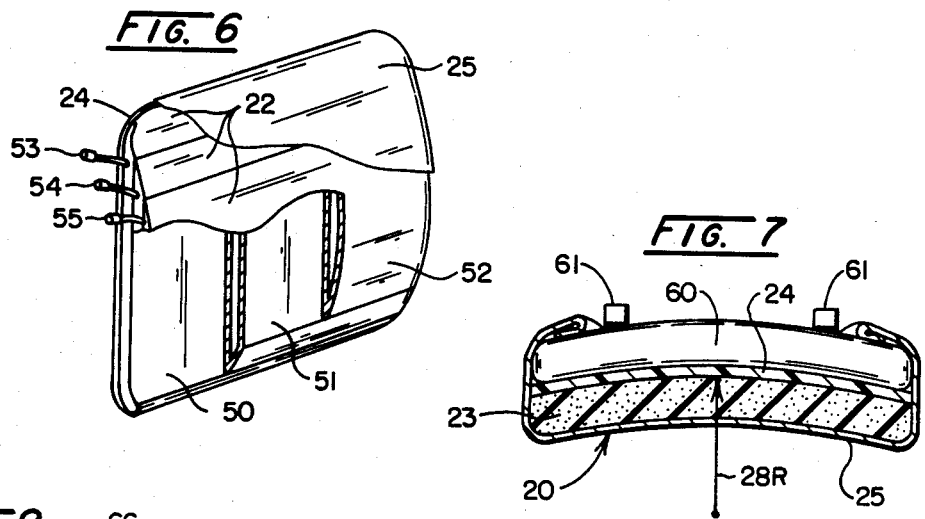
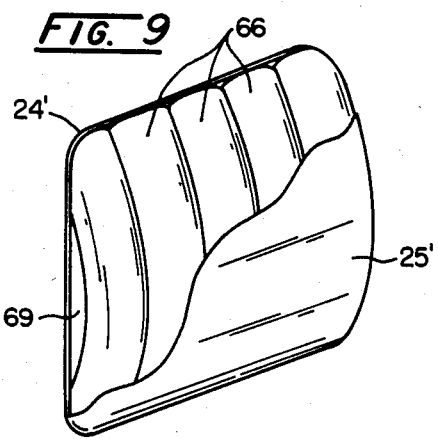
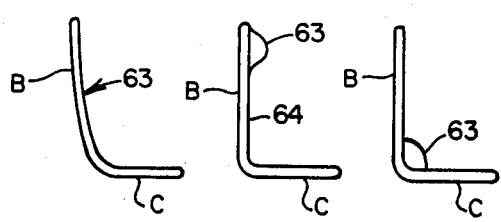

LUMBAR SUPPORT SYSTEM

TECHNICAL FIELD OF THE INVENTION

This invention relates to a portable apparatus and system for supporting the lumbar lordosis region of the back of a human being. More particularly, it relates to a system constructed for application to the back rest of a structure for unholding a human body. The structure is usually for seating.

BACKGROUND OF THE INVENTION

Back pain represents the single most costly medical investment in the United States today—over 14 million dollars annually is often quoted as the medical cost of back pain, and most medical authorities agree that most back pain is not pathologic, and much chronic back discomfort is associated with faulty posture associated with prolonged sitting.

The anterior convexity of the lumbar spine, particularly the lower lumbar and upper sacral area, is the origin of the vast majority of back problems in human beings. It is well known that any mechanical flattening of the normal lumbar curve, often called the "lumbar lordosis", aggravates or produces many of the nonspecific syndromes of the lower lumbar area. While individual human beings normally can voluntarily project this curve while standing, walking, or lying face down, they generally can not do so while sitting with their back improperly supported by a flat or concave seat back or lying flat on the back for prolonged periods of time, and such situations often introduce dynamics leading to the loss of lumbar lordosis. Sitting in a softly cushioned, or improperly designed chair, or lying face up in a supine position on a mattress with improper support defeats the body's normal protective muscular control over the lower lumbar area.

This disclosure is directed primarily to problems of upholding the human body in a seating position. But many of the objectives and concepts also have application to the supine (lying down face up position). It is expected that those concepts which are transferrable will be recognized by those familiar with the field.

Referring to FIG. 1 in the drawings, a typical cross-section of a portion of a human body on a conventional seating arrangement is shown. As shown, the body is longitudinally vertical in accepted medical terminology, meaning that the axis of the human body is considered to be longitudinal from head to foot (cephalo-caudal). Planes taken perpendicular to this longitudinal axis are termed transverse. Such terms will be applied to the similarly associated portions of the apparatus and system of the invention described herein.

In this FIG. 1, a chair designated by the letter C is diagrammatically illustrated as including a generally horizontally disposed seat S and a vertically extending back B. It will also be noted in this diagrammatically illustration that the back B is oriented at an angular relationship to the seat which is slightly graded at a right angle; for example, it is customary in most chairs to provide an angular relationship on the order of 95°-100°. It will be noted that persons seated on such a chair C will in effect have a substantially unsupported portion of the posterior of their spines, since the chair back is generally a flat planar structure and has little, if any, capability to conform with the lumbar lordosis LL and cannot provide any support. It will be also noted that the spine is shown in a correct configuration to achieve lumbar lordosis and provide proper support for body weight. Consequently, in the absence of providing a lumbar cushion system 20 of this invention, a person's spine will be effectively unsupported and that person must then rely entirely upon proper geometrical positioning of the body that must be physically maintained by a particular person in order to prevent fatigue and avoid adversely affecting the spine. Without such support, there will be a substantial tendency for fatigue and possible accompanying complications as to spinal problems due to physical inability to maintain lumbar lordosis for prolonged time periods.

Another factor to consider in attaining a proper support configuration is the relative positioning of the pelvic bone structure indicated generally at H. The spinal column extends upwardly from this pelvic bone structure and, in a seated position, the latter is preferably oriented in the illustrated position such that it is tending to incline slightly forward. This is induced through the proper body positioning as is illustrated, and results in providing a positive, stable base from which the spine, extending in a relatively vertical position, will obtain the most comfortable and optimum support for carrying of the body weight.

While the spine is relatively unsupported in case of a conventional chair C having a straight back or worse concave, it will be seen that use of a lumbar cushion system 20 of this invention will result in the proper support of the most important lumbar and upper sacral regions. In this elevational side view, it will be seen that the lumbar cushion system 20 is uniquely adapted to be located at the proper elevational position with a base surface 21 disposed in supported relationship to the forwardly facing surface of the chair back B. This then places the convex lumbar supporting surface 22 of the system in forwardly facing relationship for supporting and contacting engagement with the posterior 19 of the seated person's body. When thus vertically oriented, as indicated, and constructed with the optimum geometrical design as devised in accordance with this invention, it will be seen that this structure now provides a surface against which the posterior body surface will rest and will tend to obtain the necessary vertical support. The above summarizes the prior art. The objective is to fill the lumbar lordosis with resilient material without pressure points. Individual control of size, position, resiliency, and adaptation to existing structures are parameters this invention provides.

It will be understood in this diagrammatic illustration of the utilization of the lumbar cushion system 20 of this invention, as will be explained in greater detail hereinafter, that the structure will incorporate means for attaching or maintaining the system at a proper vertical elevation on a chair back B relative to a seated person's back. This attachment means is essential in assisting and maintaining the structure at the desired elevation and thus enable the person to move without resulting in displacement of the structure to an improper and incorrect position.

The concept of providing a lumbar support device has been considered in the past and various constructions have been patented. The prior art U.S. Pat. Nos. 1,236,517—Wemple et al., 1,667,626—Epstein, 2,060,298—Gailey, and 2,894,565—Conner disclose various constructions and apparatus means to hold a back support in place. These various patents have disadvantages in that the mechanisms are cumbersome, relatively expensive, and are lacking in adjustment features that have been found to be beneficial.

In spite of the need and previous attempts to provide proper support for the lumbar lordosis, most seating apparatus is constructed with a "main frame" configured for appearances and a "generally, comfortable look". Consequently, there remains a need for a lumbar support system that can be added to the seating arrangements that have been and continue to be sold for use. In the sense that the lumbar support system is "carried" to the existing seating; i.e., is purchased as a separate entity, brought to the site of the chair, usually at a work station, secretary position, executive chair, or in automobiles and other vehicles, it may be considered as "portable".

Because of the concern for appearances, most seat backs are either straight or convex posteriorly in the opposite direction to a proper lumbar lordosis as considered in the longitudinal direction. Not infrequently, the seat back is too short and either flat or too convex (exagerated lumbar lordosis) so that the seat back only touches the person's back at isolated positions. Many office style secretarial chairs are particularly guilty of this latter defective design, resulting in painful pressure points as well as lack of anatomic support.

In addition to the correct curvature in the longitudinal direction, a proper contour transversely at positions along the lumbar lordosis is also very important. In addition, modern seat backs have erroneously placed an anterior bulge too low where it presses on the sensitive sacrum instead of filling the lumbar lordosis.

SUMMARY OF THE INVENTION

In summary, this invention is a lumbar support system constructed primarily for application on the back rest of a human body upholding structure, the human body having a natural and generally longitudinal lumbar lordosis, comprising: (a) a flexible panel configured to attach to the back rest and to flex curvilinearly in the transverse direction to the longitudinal axis of lumbar lordosis (cephalo-caudal), the curvilinear flexure thereof providing structural rigidity in the cephalo-caudal direction of the human body on the upholding structure and lumbar support thereto; and (b) a resilient force resisting means assembled to the panel at one face thereof, and having a second face thereof with a general curvature of a predetermined lumbar lordosis, selectively positionable at the optimum lumbar supporting position of the human body upheld in the structure.

It is an object of the invention to provide that the portable lumbar support system (usually a cushion or pad) supports the empty space between the lumbar lordosis and the back of the upholding structure (primary seat). This unsupported area is thought to be responsible for fatigue during long periods of sitting even in normal persons. However, this portable pad should be anatomic and should not create any new lumps, bumps, or pressure points and should in no way deflect the person's back from the utilization and support of the full surface of the remainder of the back rest. Any characteristics of the cushion which push the person forward may then induce fatigue by restricting support to the area of the portable pad. Moreover, the pad itself should fill up the entire space between the primary seat and the lumbar lordosis. If it is restricted to a smaller area, the pressure loading on the supported surface increases proportionately and thus would create pain. It is a fault of a great many "so called" lumbar supports that they are excessively rounded or excessively hard so that the "contact patch" is too small and therefore counterproductive, and worse still, many such supports built into chairs are not located at the proper height, frequently pressing on the flat sensitive sacral area.

In the case where a secretarial chair has a back rest limited to the lumbar area, it is all the more important to fill and support the entire lumbar area, vertically.

Therefore, not only is the portable lumbar cushion concept ideal for creating proper support in a relatively flat backed seat, but also many original equipment designs will benefit from an engineered-in adjustable lumbar component. Moreover, some seats with existing but incorrect lumbar supports can be corrected by the use of the portable cushion if it is done in a prescription fashion for the type of chair, and perhaps for the individual.

Other objects and features of the present invention include:

1. A portable lumbar support cushion, or pad with interchangeable modular components permitting the user to achieve optimum comfort, function, and appearance.

2. A portable lumbar support system which utilizes a removeable smooth fitting cover which is preferably of stretchable material and which is secured to the back of the unit with a perimeter drawstring or elastic tape. This does not preclude other means of fixation such as Velcro, snaps, etc.

3. A portable lumbar support system which utilizes common flexible and resilient foam core materials anatomically shaped to fill and support the area which is not filled by the primary back rest.

4. An optional unique anatomic lumbar foam core which is adjustable for depth while maintaining anatomic contours because of a proprietary multilayer design with each layer parallel to the base plane. This permits all interchangeable sizes to be provided in one multilayer pad permitting perfect fitting to the user at low cost and with no mechanical devices.

5. A uniquely versatile system capable of being attached or fitted to a great variety of problem seating situations and existing in situ furniture, without losing the important longitudinal rigidity provided by the system of the invention.

The foregoing and other advantages of the invention will become apparent from the following disclosure in which preferred embodiments of the invention are described in detail and illustrated in the accompanying drawings. It is contemplated that variations in procedures, structural features and arrangement of parts may appear to the person skilled in the art, without departing from the scope or sacrificing any of the advantages of the invention.

DESCRIPTION OF THE DRAWINGS

FIG. 1 is a schematic elevational cross-section view of the body of a human being upheld in a seating arrangement.

FIG. 2 is a perspective view of a resilient force-resisting means or cushion forming a part of the lumbar support system of this invention.

FIG. 3 is an elevational cross-section view of the components of the lumbar support system of this invention.

FIG. 4 is an elevational view of the back of a resilient force-resisting means or cushion forming a part of this invention.

FIG. 5 is a partial perspective view of another embodiment of this invention.

FIG. 6 is a partial perspective view of still another embodiment of this invention.

FIG. 7 is a schematic plan view of a transverse section of the system of this invention attached to a typical secretarial chair back rest.

FIGS. 8a–8c are schematic longitudinal section views of chair back configurations on which the system of this invention may be used to an advantage.

FIG. 9 is a perspective view of still another embodiment of this invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

BEST MODE FOR CARRYING OUT THE INVENTION

Referring to FIG. 1 a chair C comprises a back B and a seat S which supports a human being H in seated position. The human being is seated with his/her spine in a preferred form of lumbar lordosis with vertebrae T9–T12 and L1–L5 in the preferred position. Such a position places the spine in the preferred shape, with a lumbar support system 20 in position between the person's back 19 and the seat back B.

Referring to FIGS. 2 and 3, the lumbar support system includes a base surface 21 generally straight and vertical in cross-sectional elevation, and a support surface 22 having the longitudinal shape of a preferred lumbar lordosis formed to fit in mating contact with the preferred and ideal shape of the person's back 19 in the seated position on the chair C. The system includes a resilient portion or cushion 23 assembled to a flexible panel 24. The resilient portion 23 is preferably constructed of a plastic foam, such as polyurethane.

While the resilient force resisting means 23 may be connected directly to the panel by an adhesive, it is preferably retained in position by a cloth or other material cover 25.

The panel 24 has, in general shape, the height in the vertical direction of the vacant space in the lumbar lordosis region of the back of a human being. In the horizontal direction, the size and configuration is as convenient for the particular seat back B to which it is intended to be attached. The cover 25 may be elastic cloth and generally shaped to fit over and conform to the exterior of the panel 24 and cushion 23 in their assembled position, shown in FIG. 3. The assembly as a unit is retained in position by an elastic border 26, or a draw string 27, or Velcro ® flaps.

Velcro ® is a trademark name of cloth-like material having a surface that is constructed with a plurality of oblong indentations which adhere to hook-like formations of the material. These materials are commonly marketed under the name of Velcro ®, a registered trademark of the American Velcro Corporation of New York, N.Y.

The panel 24 is semi-rigid and flexible, being formed of a material and thickness to provide a rigidity sufficient to retain it in a self-supporting panel-like shape when manufactured and transported, but flexible enough to be formed by manually applied forces to take a curvilinear shape 28 R in the direction transverse to the longitudinal axis of lumbar lordosis as shown in FIG. 1.

The panel is preferrably provided with apertures 30, typically arranged in a vertical row on either side of the panel 24. A strap 31 capable of being fastened with a buckle 32 may be provided through the apertures 30 for the purpose of fastening the panel 24 and the lumbar support system 20 as a whole to a seat back B as convenient and at the place of use in situ.

Alternatively, apertures 33 may be provided for straps, or elastic cords or rubber belts or grommets 34 and buckles 35 in another direction, such as horizontal.

As a further alternative, panels of hook and lattice materials such as Velcro strips 36 may be provided at convenient locations for the attachment of the panel 24 to a seat back B which is provided with matching fabric.

It will be seen, that the panel 24 may be provided with all or an alternative selection of the above described attachment anchor means, so that the lumbar support system of this invention may be conveniently attached at the place of use in situ, with the anchor means being selected according to the kind and type of back rest encountered.

In operation and use of the lumbar support system 20, when constructed according to the above description, panel 24 and the foam cushion 23 are flexed to take a matching configuration to the back rest B. The back rest B in all normal conventional seating is provided with a curvilinear shape in the transverse direction opposite to the longitudinal axis of lumbar lordosis of a human body upheld therein. When the panel 24 is fastened in position on the back B, the panel is flexed to conform to this curvilinear shape. Flexure of the panel on this vertical axis configures the panel in the general structural shape of a columnar beam causing the panel to become rigid along the axis. This rigidity on the longitudinal axis of lumbar lordosis insures that the support system holds to a preferred shape 22 to properly support the back 19 of each person. By this combination of flexible panel 24, and resilient force resisting means 23, proper shape of lumbar lordosis is provided from the upper end 40, to the lower end 41 and there between. Because the panel 24 has been flexed to the rigid longitudinal beam shape, the ends 40 and 41 are prevented from bending and allowing the proper support to be lost at the critical end areas of the upper curve in the longitudinal (cephalo-caudal) direction.

On the other hand, if some slight flexure is desired at the ends, the foam cushion 23 may be constructed to extend slightly beyond the ends of the panel 24 to give a further rounding effect.

In order to provide further versatility in the lumbar support system of this invention, the resilient force resisting means 23 may be constructed according to the embodiment of the invention shown in FIG. 5. In this embodiment, the cushion 23 comprises overlaid juxtaposed segments 45, 46, and 47; each of which comprise a portion of the total shape of the surface 22 of the system 20. By the appropriate selection of the number of panels the size of the system may be adjusted to fit the size of the person who will be using the system 20. If a smaller person is the user, the back panel 45 may be omitted and the cover tightened by draw string 27, and the elastic shape 26 of the cover 25.

In addition, the segments 45, 46, and 47 may be constructed with foams having different resiliences (i.e., "harder or softer") from a "standard" or from each other. By this means custom fitting may be provided for comfort or therapeutic reasons.

In the embodiment of FIG. 5, the plurality of juxtaposed segments 45, 46, and 47 are retained in mutually supporting engagement with each other by the panel in cooperation with the cover and the cover confines the segments to the configuration of the panel 24.

Referring to FIG. 6, in still another embodiment, the foam segments 45, 46, and 47 of FIG. 5, are replaced by inflatable segments 50, 51, and 52 which are juxtaposed and configured to provide-in composite-the correct lumbar lordosis shape 22. Each segment is inflated to a selected degree by a valve 53, 54, or 55. Segments may be typically constructed of resilient thin walled vinyl or rubber or other non-porous material having the degree of resilience needed to provide the degree of comfort and therapeutic effect selected.

Referring to FIG. 7 a secretarial chair-type back rest 60 is carried by frame members 61. The back rest 60 has a transverse concave curvature 28 R. The panel 24 is attached to the back rest 60 and flexed to conform to the curvature 28 R. The cushion 23 is assembled to the panel 24 by the cover 25, when it is desireable to give the assembly a unitary eye pleasing appearance, otherwise the straps and buckles or Velcro fastenings are used. In the case of a deep concavity (arc) in the horizontal plane (transverse), both may be used.

Because of the columnar rigidity created in the panel 24 by the curvature flexed therein, the system 20 provides the proper longitudinal cephalo-caudal shape to the cushion 23 irrespective of the shape of the back rest either in the longitudinal direction or in other directions that do not effect the curvature 28 R. By this construction, the system provides a proper longitudinal shape when assembled in situ under a wide variety of situations.

FIG. 8a shows a back rest having a typical "comfortably appearing" chair configuration having an improper concavity 63 in the cephalo-caudal direction. FIG. 8b shows another typical improper chair configuration having a head rest 63 and a straight back 64. FIG. 8c shows a very common padding 63 mistakenly located too low over the sacral area which forces the hips forward leaving the lumbar lordosis unsupported while creating a painful pressure point over the sacrum.

An advantage of this invention is the capability of correcting the improper poor seating arrangements shown in FIGS. 8a, 8b, and 8c.

FIG. 9 shows another embodiment of this invention in which inflatable longitudinal tube segments 66 are assembled on a panel 24' with a cover 25' and attached to a chair back rest 69. Because of the resilience of the segments 66 and their longitudinal support on the panel 24' which has been flexed to provide longitudinal rigidity, the segments take on an appropriate lumbar lordosis configuration when pressed against the back of a user.

As an additional means of providing convenience when the lumbar support system of this invention is provided at the place of use in situ, panel 24 may comprise layered or interchangeable segments. For instance, two or more substantially identical panels may be provided and used in the assembly of the system to provide alternative selection of the rigidity and strength of the system; or interchangeable vertically shorter panels may be provided to give greater flexibility of the lower portion of the support. In assembly, the identical panels can be laid one upon the other and the straps passed through the matching apertures.

It is herein understood that although the present invention has been specifically disclosed with the preferred embodiments and examples, modification and variations of the concepts herein disclosed may be resorted to by those skilled in the art. Such modifications and variations are considered to be within the scope of the invention and the appended claims.

I claim:

1. A lumbar support system constructed for application on the back rest of a human body upholding structure, the human body having a natural and generally longitudinal lumbar lordosis, comprising:
   a. A semi-rigid and preformed flexible planar panel element constructed and configured to attach to the back rest, and to extend essentially to the periphery of the support system, to flex curvilinearly in the transverse direction to the longitudinal axis of lumbar lordosis, the curvilinear flexure thereof providing a columnar beam structural longitudinal rigidity in the cephalo-caudal direction of the human body on the upholding structure, and proper lumbar support thereto, from the upper end to the lower end and there between; and
   b. A resilient force resisting means constructed of a material less rigid than said flexible panel, assembled to the panel at one face thereof, and having a second surface thereof with a general curvature of a predetermined lumbar lordosis, selectively positionable at the optimum lumbar supporting position of the human body upheld in the structure.

2. A lumbar support system according to claim 1 wherein the upholding structure is constructed to maintain the human body in a seating position.

3. A lumbar support system according to claim 2 wherein the seating position upholding structure is constructed as a separate entity and the panel is attached thereto at the place of use in situ.

4. A lumbar support system according to claim 3 wherein the resilient force resisting means is a cushion contained in an conforming cover.

5. A lumbar support system according to claim 4 wherein the cover envelops the edges of the panel.

6. A lumbar support system according to claim 5 wherein the panel is provided with anchor means constructed to engage the back rest of the seating structure and uphold the panel and cushion thereon.

7. A lumbar support system according to claim 6 wherein the anchor means comprise flexible straps passing through apertures in the a panel, encircling and engaging the back rest.

8. A lumbar support system according to claim 6 wherein the anchor means comprises a Velcro strip or sheet attached to the panel and positioned to engage the surface of the back rest when the lumbar support system is connected to the back rest.

9. A lumbar support system according to claim 4 wherein the cushion comprises a plurality of juxtaposed segments retained in mutually supporting engagement with each other by the cover and is constructed for selective removal of at least one segment to adjust the thickness of the cushion and/or the shape of the lumbar lordosis of the surface of the cushion.

10. A lumbar support system according to claim 9 wherein the juxtaposed segments comprise resilient foam material.

11. A lumbar support system according to claim 9 wherein the segments comprise inflatable resilient hollow pads.

12. A lumbar support system according to claim 1 wherein the panel is constructed to receive and engage additional support panel segments that are capable of being selectively added to increase the rigidity of the panel.

13. A lumbar support system according to claim 4 wherein the cushion extends below the bottom extremity of the panel providing for curvature of the cushion at the position of the lumbar lordosis.

14. A lumbar support system according to claim 1 wherein the resilient force resisting means comprises a plurality of longitudinally arranged inflatable tube segments.

* * * * *